US012396696B2

United States Patent
Mayfield et al.

(10) Patent No.: US 12,396,696 B2
(45) Date of Patent: Aug. 26, 2025

(54) PHYSIOLOGICAL MODELING OF MULTIPHASE INTRA-ARTERIAL CT ANGIOGRAPHY FOR HEPATIC EMBOLIZATION THERAPY

(71) Applicant: UNIVERSITY OF SOUTH FLORIDA, Tampa, FL (US)

(72) Inventors: John David Mayfield, Tampa, FL (US); Ghassan Elias El-Haddad, Tampa, FL (US); Jonathan Michael Ford, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 18/727,034

(22) PCT Filed: Nov. 20, 2023

(86) PCT No.: PCT/US2023/080621
§ 371 (c)(1),
(2) Date: Jul. 5, 2024

(87) PCT Pub. No.: WO2024/108231
PCT Pub. Date: May 23, 2024

(65) Prior Publication Data
US 2024/0415478 A1    Dec. 19, 2024

Related U.S. Application Data

(60) Provisional application No. 63/384,325, filed on Nov. 18, 2022.

(51) Int. Cl.
*A61B 6/50* (2024.01)
*A61B 6/00* (2006.01)
(Continued)

(52) U.S. Cl.
CPC ............ *A61B 6/504* (2013.01); *A61B 6/5217* (2013.01); *G06F 30/10* (2020.01); *G16H 50/20* (2018.01); *G16H 50/50* (2018.01)

(58) Field of Classification Search
CPC ....... A61B 6/504; A61B 6/5217; A61B 6/463; A61B 6/507; A61B 6/545; A61B 6/032;
(Continued)

(56) References Cited

U.S. PATENT DOCUMENTS

| | | | |
|---|---|---|---|
| 11,566,543 B2 * | 1/2023 | Janicki | F23G 5/04 |
| 2003/0017612 A1 * | 1/2003 | Gerber | A61P 35/00 |
| | | | 562/606 |

(Continued)

FOREIGN PATENT DOCUMENTS

| WO | 2021/046389 A1 | 3/2021 |
|---|---|---|
| WO | 2024/108231 A1 | 5/2024 |

OTHER PUBLICATIONS

International Search Report of Related PCT/US2023/080621, mailed Feb. 9, 2024, 3 pages.

(Continued)

*Primary Examiner* — Sanjay Cattungal
(74) *Attorney, Agent, or Firm* — Husch Blackwell LLP (57) ABSTRACT

Systems and methods are provided herein for determining areas of low blood flow, low blood perfusion, suboptimal treatment perfusion, and/or likelihood of tumor recurrence. For example patient-specific methods are provided for identifying areas of low perfusion in an anatomy of interest (such as a vascular region). Angiography data corresponding to the anatomy of interest can be used to generate a modified three-dimensional (3D) model of the anatomy of interest, which represents a fluid flow system exhibiting variant flow patterns. The model can take into account patient-specific data to simulate physical characteristics of the fluid flow (Continued)

system. This provides for accurate determination of localized areas of low perfusion, which can be indicative of potential tumor recurrence.

19 Claims, 5 Drawing Sheets
(3 of 5 Drawing Sheet(s) Filed in Color)

(51) Int. Cl.
  *G06F 30/10* (2020.01)
  *G16H 50/20* (2018.01)
  *G16H 50/50* (2018.01)
(58) Field of Classification Search
  CPC ........ G06F 30/10; G16H 50/20; G16H 50/50; G16H 30/40; G06T 7/0012; A61P 35/00
  See application file for complete search history.

(56) References Cited

U.S. PATENT DOCUMENTS

| | | | |
|---|---|---|---|
| 2005/0238727 A1* | 10/2005 | Cagnoni | A61P 35/04 600/1 |
| 2007/0259966 A1* | 11/2007 | Cagnoni | A61P 35/00 514/716 |
| 2007/0299136 A1* | 12/2007 | Johnson | A61P 9/02 562/405 |
| 2010/0009930 A1 | 1/2010 | Sherman et al. | |
| 2014/0053837 A1* | 2/2014 | Klein | A61M 16/0051 128/203.14 |
| 2014/0249399 A1* | 9/2014 | Sharma | G06T 7/0012 600/407 |
| 2015/0248758 A1* | 9/2015 | Pautot | G06T 7/0016 382/131 |
| 2016/0000913 A1* | 1/2016 | Haaga | A61K 31/44 424/133.1 |
| 2016/0045841 A1* | 2/2016 | Kaplan | B09B 5/00 429/49 |
| 2016/0128601 A1* | 5/2016 | Kennedy Mcconnell | A61B 5/055 600/431 |
| 2017/0018081 A1* | 1/2017 | Taylor | A61B 6/507 |
| 2017/0071496 A1 | 3/2017 | Gillies et al. | |
| 2017/0143427 A1* | 5/2017 | Grady | G06T 7/0012 |
| 2018/0042473 A1* | 2/2018 | Wang | A61B 5/0066 |
| 2018/0067120 A1 | 3/2018 | Dylla et al. | |
| 2018/0328914 A1* | 11/2018 | Devi | G01N 33/5011 |
| 2019/0213738 A1* | 7/2019 | Wang | G06T 5/50 |
| 2019/0355118 A1* | 11/2019 | Zilberstien | A61B 6/5217 |
| 2020/0038586 A1* | 2/2020 | Chomas | A61B 5/027 |
| 2020/0410683 A1* | 12/2020 | Hu | G06T 7/0016 |

OTHER PUBLICATIONS

Written Opinion of Related PCT/US2023/080621, mailed Feb. 9, 2024, 6 pages.
Haller et al. "Arterial spin labeling perfusion of the brain: emerging clinical applications." Radiology 281.2 (2016): 337-356.

* cited by examiner

PHYSIOLOGICAL MODELING OF MULTIPHASE INTRA-ARTERIAL CT ANGIOGRAPHY FOR HEPATIC EMBOLIZATION THERAPY

CROSS-REFERENCE TO RELATED APPLICATIONS

This application is a national phase of the pending International Application PCT/US2023/080621 filed on Nov. 20, 2023, which claims priority under 35 U.S.C. § 119 to U.S. Provisional Patent Application No. 63/384,325 filed on Nov. 18, 2022, the entire content of each of which is incorporated herein by reference.

STATEMENT REGARDING FEDERALLY SPONSORED RESEARCH

Not applicable.

BACKGROUND

In interventional oncology, angiographic scans (such as Computed Tomography Angiography (CTA)) are often used to guide treatment plans. For example, where treatment may include radioembolization, angiography can be used for mapping anatomy for treatment of hepatic tumors. However, predicting response to the treatment can be difficult.

Presently, to predict treatment response, a surrogate is often used, attached to a macroaggregated albumin. For example, a macroaggregated albumin is used to determine the hepatopulmonary shunt and as a surrogate for radiomicrospheres in patients receiving radioembolization. For the macroaggregate albumin, the challenge is obtaining accuracy as a surrogate for metastatic lesions, namely metastatic neuroendocrine tumors that can be hyper or hypo-vascular. More generally, other existing methods similarly lack the ability to predict response in terms of the extent to which a given treatment will perfuse to the locality of interest and, thereby, cause a positive outcome for the patient.

SUMMARY

The following presents a simplified summary of one or more aspects of the present disclosure, in order to provide a basic understanding of such aspects. This summary is not an extensive overview of all contemplated features of the disclosure, and is intended neither to identify key or critical elements of all aspects of the disclosure nor to delineate the scope of any or all critical elements of all aspects of the disclosure nor to delineate the scope of any or all aspects of the disclosure. Its sole purpose is to present some concepts of one or more aspects of the disclosure in a simplified form as a prelude to the more detailed description that is presented later.

In some aspects, the present disclosure can provide a patient-specific method for identifying areas of low perfusion in an anatomy of interest, the method comprising: receiving angiography data corresponding to the anatomy of interest within a patient; generating a three-dimensional (3D) model of the anatomy of interest, based on the angiography data; modifying the 3D model to represent a fluid flow system exhibiting variant flow patterns; ascribing physical characteristics to a simulation of the fluid flow system based on patient-specific data; determining at least one low perfusion area of the anatomy of interest; and outputting to a user an indication of potential tumor recurrence to a user display, based on determination of the at least one low perfusion area.

In another aspect, the present disclosure can provide a system that provides information to a user (e.g., a healthcare professional such as an oncologist) with an indication of treatment performance and/or likelihood of recurrence for a tumor of interest. The system may comprise: a data link connected to receive angiography data for an anatomy of interest, acquired via an angiography scan of a patient; a medical image database connected to the data link and configured to store the angiography data; and a server or other processing device connected to the database, that runs software programmed to: obtain a three-dimensional computer model for a portion of the anatomy of interest comprising at least one suspected tumor, based on the angiography data; define a fluid flow model for the portion of the anatomy of interest, the fluid flow model configured to simulate perfusion within the portion of the anatomy of interest based on a blood viscosity estimation, a blood flow estimation, and a vascular wall elasticity estimation; determine whether a localized area of low perfusion within the portion of the anatomy of interest corresponds to a location of the suspected tumor and, if so, identify the suspected tumor as having a likelihood of recurrence; and output a mapping to a user via a display device, showing at least one of the localized area of low perfusion or the likelihood of recurrence for the suspected tumor, within the portion of the anatomy of interest.

These and other aspects of the disclosure will become more fully understood upon a review of the drawings and the detailed description, which follows. Other aspects, features, and embodiments of the present disclosure will become apparent to those skilled in the art, upon reviewing the following description of specific, example embodiments of the present disclosure in conjunction with the accompanying figures. While features of the present disclosure may be discussed relative to certain embodiments and figures below, all embodiments of the present disclosure can include one or more of the advantageous features discussed herein. In other words, while one or more embodiments may be discussed as having certain advantageous features, one or more of such features may also be used in accordance with the various embodiments of the disclosure discussed herein. Similarly, while example embodiments may be discussed below as devices, systems, or methods embodiments it should be understood that such example embodiments can be implemented in various devices, systems, and methods.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

The detailed description set forth below in connection with the appended drawings is intended as a description of various configurations and is not intended to represent the only configurations in which the subject matter described herein may be practiced. The detailed description includes specific details to provide a thorough understanding of various embodiments of the present disclosure. However, it will be apparent to those skilled in the art that the various features, concepts and embodiments described herein may be implemented and practiced without these specific details. In some instances, well-known structures and components are shown in block diagram form to avoid obscuring such concepts.

As described herein, the inventors have determined that angiography data can be used to model blood flow in patients with various pathologies (e.g., malignant liver lesions, cancer, tumors, etc.), which can in turn help predict patient-specific efficacy of a given treatment (e.g., delivered orally, by injection, or other fashion dependent on distribution to an anatomy of interest by blood flow). For example, the embodiments described herein might be used to predict the degree of deposition of microspheres, allowing for better radiation planning and outcomes for radioembolization treatments.

The visualization of three-dimensional blood flow behavior on computed tomography angiography (CTA) can help to identify potential regions of decreased response to radioembolization, which can assist in altering treatment planning. If a tumor's saturation is deemed suboptimal based upon the model, a patient may find a greater treatment response with alternative therapies, such as percutaneous ablations. Previous attempts of translating angiographic images into realistic models ranged from two-dimensional flow diagrams to three-dimensional rigid wall, synthetic structures. The approach described herein includes a unique method of analyzing multiphasic intra-arterial CT angiograms to identify low-flow areas on a three-dimensional model. This approach may allow areas of decreased flow to be assessed for an increased risk of tumor recurrence after radioembolization.

Hardware Configurations and Embodiments

Systems that implement the embodiments described herein may take a variety of different configurations. In some configurations, these systems may implement visualization of intra-arterial CT angiograms through computational resources connected to CT imaging platforms, such as a specialized PACS (Picture Archiving and Communication System) system in which processors and data stores are configured to rapidly process, manage, store, recall, and display medical images such as DICOM-based images and data. In one example, a PACS may comprise a connection to an imaging device (such as a CT scanner), a PACS server that runs specific software for storing and managing medical images and data (which often includes a medical imaging database for storing the images/data) that allows for more rapid acquisition and storage of imaging data from a scanner (imaging device) as well as processing of that data. A PACS system may also include a workstation that is configured to run a PACS client and is used by a healthcare professional (such as a radiologist) to view and manipulate the images and imaging data.

Figure 4:
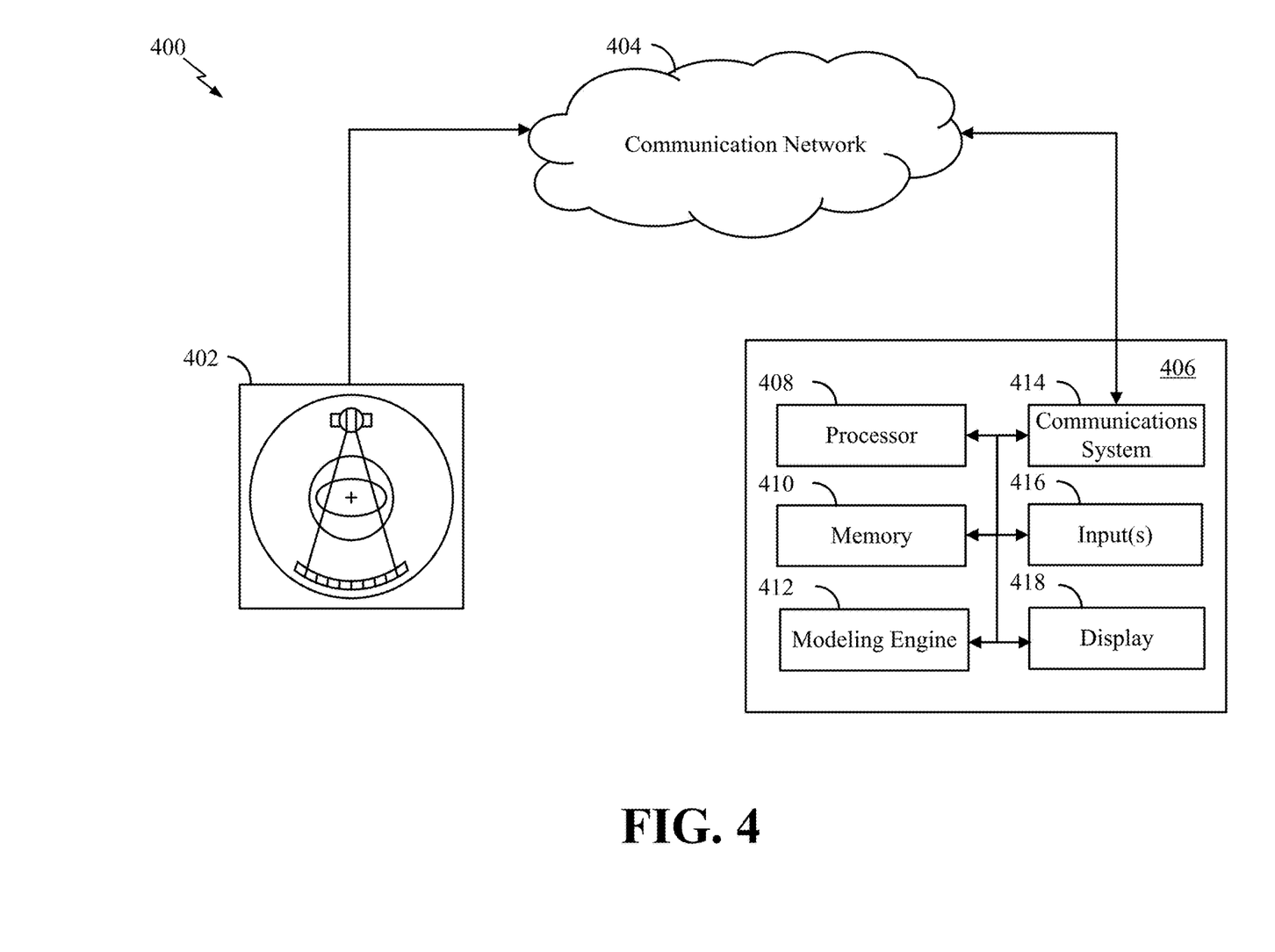
FIG. 4 is a block diagram conceptually illustrating an artery modeling system according to some embodiments.

FIG. 4 is a block diagram that conceptually illustrates one embodiment of a system for visualization of three-dimensional blood flow behavior via CTA image data. As shown in FIG. 4, a computing device 406 can receive angiography data from a CT scanner 402. The computing device 406 may comprise a PACS server or other similar server that is configured for efficient acquisition and storage of CT scanner data, such as CTA data. The CTA data can be sent to the computing device 406 directly from the CT scanner via a high speed link, or sent from a remote location (e.g., a hospital, a laboratory, etc.) via another type of data link such as communication network 404. In some examples, the angiography data can include one or more metrics related to an artery.

The computing device 406 can further include, or be connected to, a processor 408. In some embodiments, the processor 408 can include or comprise any suitable hardware processor of combination of processors, such as a central processing unit (CPU), a graphics processing unit (GPU), an application specific integrated circuit (ASIC), a field-programmable gate array (FPGA), a digital signal processor (DSP), a microcontroller (MCU), a cloud resource, etc. In some embodiments, the computing The computing device 406 can further include, or be connected to, a memory 410. The memory 410 can include or comprise any suitable storage device(s) that can be used to store suitable data (e.g., CT angiography data, etc.) and instructions that can be used, for example, by the processor 408. The memory may be a memory that is "onboard" the same device that receives the radar data, or may be a memory of separate device connected to the computing device 406. Methods for modeling an artery may operate as independent processes/modules, such as a separate modeling engine 412 that runs on the same processor 408 or a specialty processor (such as a GPU) that achieves greater efficiency in processing the angiography data, as described below. The memory 410 can include any suitable volatile memory, non-volatile memory, storage, or any suitable combination thereof. For example, memory 410 can include random access memory (RAM), read-only memory (ROM), electronically-erasable programmable read-only memory (EEPROM), one or more flash drives, one or more hard disks, one or more solid state drives, one or more optical drives, etc.

In further examples, computing device 406 can receive or transmit information and/or any other suitable system over a communication network 404. In some examples, the communication network 404 can be any suitable communication network or combination of communication networks. For example, the communication network 404 can include a Wi-Fi network (which can include one or more wireless routers, one or more switches, etc.), a peer-to-peer network (e.g., a Bluetooth network), a cellular network (e.g., a 3G network, a 4G network, a 5G network, etc., complying with any suitable standard, such as CDMA, GSM, LTE, LTE Advanced, NR, etc.), a wire network, etc. In one embodiment, a communication network 404 can be a local area network, a wide area network, a public network (e.g., the Internet), a private or semi-private network (e.g., a corporate or university intranet), any other suitable type of network, or any suitable combination of networks. Communications links shown in FIG. 35 can be any suitable communications link or combination of communications links, such as wire links, fiber optics links, Wi-Fi links, Bluetooth links, cellular links, etc.

In further examples, the computing device 406 can further include a display device 418 and/or one or more inputs 416. In one embodiment, the display 418 can include any suitable display devices, such as a computer monitor, a touchscreen, a television, an infotainment screen, etc. to display the angiography summary. The display may present images to the user (e.g., a radiologist, pathologist, cardiologist, etc.) via a specialized interface for 3D CT image handling. In further embodiments, and/or the input(s) 416 can include any suitable input device (e.g., a keyboard, a mouse, a touchscreen, a microphone, etc.).

Example Processes

Figure 5:
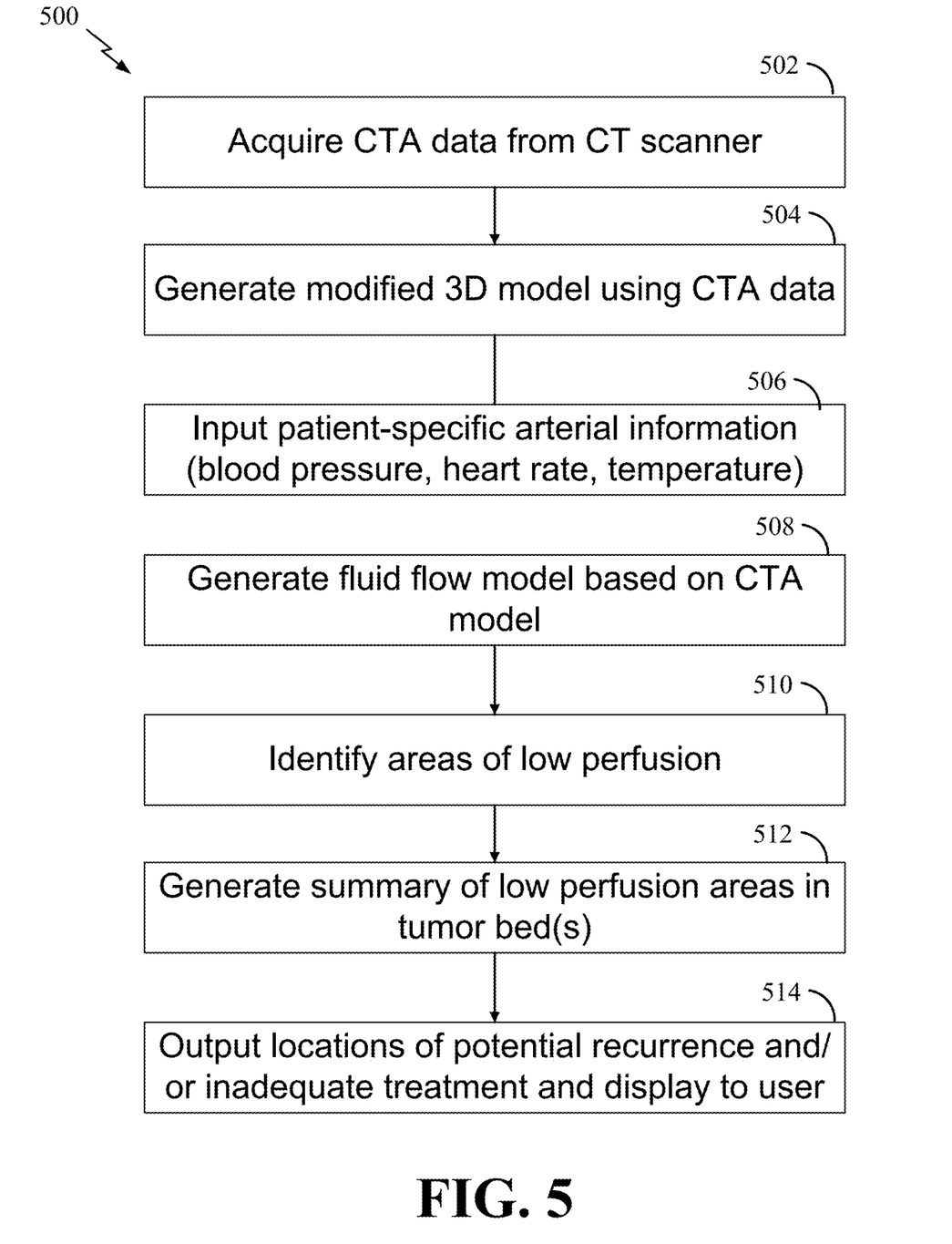
FIG. 5 is a flowchart illustrates an example process for an artery modeling system according to some embodiments.

In some embodiments, methods or techniques may be provided for 3D visualization of arterial blood flow from CT angiography data. Referring now to FIG. 5, a flowchart is shown showing an example of a process 500 for generating and displaying such a visualization for purposes of aiding healthcare teams in assessing effectiveness of current treatment and whether an alternative or additional treatment, or a treatment modification, may be beneficial.

At block 502, the process 500 may begin with acquisition of angiography data, such as CTA data from a CT scan. Other angiography modalities that could also be utilized include magnetic resonance angiography (MRA) or other volumetric angiography data. In the illustrated example, the CTA data may be CTA data that was acquired via a CT angiography scan, and may be acquired directly from the scanner as the scan is being performed, or from a memory/database at a subsequent time. In some embodiments, the CTA scan may be a modified CT angiography scan that is increased in duration in order to acquire a time period that covers one or several heartbeat cycles, so that blood flow cycles can be observed at the artery of interest. In some embodiments, the time period may be 6 s, 8 s, 10 s, 12 s, 14 s, or similar durations. The duration of the scan can be determined according to the pathology and/or anatomy of interest. In other words, given the location, dimension, tissue type, and other factors, it may take longer or shorter periods of time to visualize perfusion of a contrast agent or therapeutic. And, depending on tumor pathology, the phase of interest to be detected may be early or late. In some embodiments, an initial injection and scan may be utilized to determine on a patient-specific basis what the proper duration is to scan for this specific patient, for this specific anatomy of interest. For example, a 50/50 saline-contrast agent mix may be manually injected and monitored under fluorescence to localize for a CT scan, and during this initial injection timing information can be obtained in addition to localization. For such extended periods, an automated pump injector (or similar device) may be used to cause an extended duration of contrast agent introduction through the artery of interest.

At block 504, a modified 3D model of the artery or other anatomy of interest may be generated. The 3D model will be used to simulate patient-specific behavior of a given arterial anatomy of interest, in terms of blood flow, treatment perfusion and/or other behavior.

In some embodiments, the model may be a 3D mesh geometry that is further processed and modified to mimic a fluid flow system. For example the 3D model may be smoothed to eliminate artifacts and create generally smooth arterial walls that are modeled as empty "pipes" or "tubes" for purposes of modeling fluid flow. And, nearby arteries and other anatomies that are not in a fluid path to/from the arteries of interest (e.g., the arteries containing tumors or other disease indicator) can be removed. At the end of the anatomy of interest, the model can be modified to mimic inflow/outflow apertures, to allow for modeling blood flow through the "system." In some embodiments, the CTA data can be imported into a DICOM image processing software such as Mimics to generate a 3D model, and then modified in the same or a separate software package (such as 3 Matic) that allows for modification of the 3D model as a CAD object.

At block 506, patient-specific information can then be entered to into the modeling software to give the 3D model physical attributes that make it a more accurate simulation of the specific patient from whom the CTA scan data was obtained. By making a more accurate simulation, a "precision medicine" approach can be taken to modify the patient's treatment plan to account for specific problem areas (as further described below). In various embodiments, patient-specific information is used to inform how a 3D fluid flow simulator presents behavior of the fluid flow system model. For example, blood can be more accurately simulated using attributes like blood pressure, heart rate, temperature, etc. Similarly, response of arterial tissue to blood flow/pressure can also be more accurately modeled, as further described below.

The viscosity and elasticity of the arterial wall can be modeled using Hooke's Law. The vessel walls' responses to internal pressure changes can be described in the following first order, non-homogenous differential equation:

$$\sigma = E_1 \varepsilon + E_2 \frac{d\varepsilon}{dt} \quad (1)$$

where the stress, $\sigma$, is dependent on the rate of strain, $$\frac{d\varepsilon}{dt}.$$

For compliance of the vessel wall, experimental values of compliance were used.

Given Newton's First Law:

$$\sum F_x = 0 \text{ such that} \quad (2)$$

$$P_0(2r_0)L + 2S_h(r_0 - r_i)L = P_i(2r_i)L$$

$$S_h(r_0 - r_i) = P_i r_i - P_0 r_0 \Rightarrow S_h h \quad (3)$$

and assuming only small strains, $$\left|\frac{dr}{r}\right| << \left|\frac{dP}{2P}\right|: \quad (4)$$

$$E\frac{dr}{r} = \frac{r^2 dP}{r_0 h_0}$$

$$\int_{P_0}^{P} dP = Er_0 h_0 \int_{r_0}^{r} \frac{dr}{r^3} \Rightarrow P - P_0$$

$$= \frac{Er_0h_0}{2}\left[\frac{1}{r_0^2} - \frac{1}{r^2}\right] + c$$

$$= \frac{Er_0h_0}{2}\left[1 - \frac{A_0}{A}\right] \quad (5)$$

where $A_0$ is the initial cross-sectional area of the vessel and A is the area of the vessel at time, t. The ratio of the two can be expressed as:

$$\frac{A}{A_0} = \left[1 - \frac{(P - P_0)2r_0}{Eh_0}\right] \quad (6)$$

Since $$\frac{(P - P_0)2r_0}{Eh_0}$$

is less than 1, it can be expressed in polynomial form:

$$\frac{A}{A_0} = 1 + C_1(P - P_0) + [C_1(P - P_0)]^2 + [C_1(P - P_0)]^3 + \quad (7)$$

To find the resultant cross-sectional area, the initial condition can be redistributed:

$$A = A_0 + A_0C_1(P - P_0) + A_0[C_1(P - P_0)]^2 + A_0[C_1(P - P_0)]^3 + \quad (8)$$

The change in cross-sectional area with respect to pressure, P, can be determined by taking the derivative of equation (8):

$$\frac{dA}{dP} = A_0C_1 + A_0C_1^2 2(P - P_0) + A_0C_1^3 3(P - P_0) + \ldots \quad (9)$$

Given that the $C_1$ constants can be small, the compliance can be estimated as:

$$C = \frac{dA}{dP} \approx A_0C_1 = \frac{2\pi r^3}{Eh_0} \quad (10)$$

To simulate the pressure-strain modulus, the ratio of the pressure change to the normalized diameter, d, change, as discussed above, is as follows (with $E_P$ as the pressure-strain modulus):

$$E_P = \frac{P_{max} - P_{min}}{(d_{max} - d_{min})/d_{avg}} (2\pi r\_0^\wedge 3)/(h\_0\pi dm) \cdot \quad (12)$$

$$2((P\_max - P\_min)/(d\_max - d\_min))$$

$$= 2\frac{r_0^2}{h_0} \cdot \left(\frac{P_{max} - P_{min}}{d_{max} - d_{min}}\right) 0 \cdot E\_P \quad (13)$$

Within the lumens of the arteries, it is also beneficial in some embodiments to more precisely model blood behavior. Blood viscosity, µ, can be described through calculating the shear rate, $$\frac{d\gamma}{dt},$$

which is equivalent to $$\frac{v}{h}$$

where v is the velocity of the fluid of the outer cylinder in a viscometer dividing the gap in the cylinders, h. The wall shear stress, τ, can then be described as:

$$\tau = \mu\frac{d\gamma}{dt} = \frac{\mu(r\omega)}{h} \quad (14)$$

The average values for these quantities can vary, however it is recognized that the blood viscosity can be approximated as 0.0035 Ns/m². The blood's density, rho, can also be approximated as 1060 kg/m³ and the mean arterial velocity, vmean, can be approximated as 20 cm/s (for example, 100-130 ml/min per 100 g of liver, 30 ml/min per kilogram of body weight). Reynold's number, Re, is then expressed as:

$$Re = \frac{\rho vd}{\mu} \quad (15)$$

In the inventors' experiments, Eulerian approaches proved more advantageous than Lagrangian, as Lagrangian modeling tends to rely more on particle-driven computational flow dynamics. Taking the Eulerian approach is, thus, more rigorous and the fluid modeled can thus be discretized, integrate particle interactions, and take into account pulsatility of the fluid. In addition, the inventors have determined that modeling blood flow as a standard laminar flow is sufficient, so long as the anatomy of interest is not proximate to the tip of the microcatheter infusing the treatment/contrast agent (which can introduce some turbulence). To model the fluid flow that undergoes pulsations, the Womersley Number, α, was utilized, which describes the relationship between oscillatory inertia and viscous momentum and includes the variable of periodicity $$\alpha = \sqrt{\frac{\rho U\omega L}{\mu\left(\frac{U}{L^2}\right)}} = L\sqrt{\omega/v} \quad (16)$$

where ρ is density, U is kinematic velocity, ω is frequency of pulsation, and μ is dynamic viscosity. Pulsatility has been studied in rigid channels described as the change of the axial velocity, u, with respect to radial coordinate, r, time.

$$\frac{\partial u}{\partial t(r,t)} = -\frac{1}{P}\frac{\partial P}{\partial x} + \frac{\mu}{P}\left(\frac{\partial^2 u}{\partial r^2} + \frac{1}{r}\frac{\partial u}{\partial r}\right) \quad (17)$$

The pressure, P, is the force across the cross-sectional area and μ is the dynamic viscosity as described above. The pressure gradient, $$\frac{\partial P}{\partial x},$$

can be restated as:

$$\frac{\partial P}{\partial x} = Ae^{i\omega t} \quad (18)$$

where ω is the angular velocity of the oscillating pressure, thus letting $$u(t) = ue^{i\omega t} \quad (19)$$

the substituting (17) into (19) yields $$\frac{\partial^2 u}{\partial r^2} + \frac{1}{r}\frac{du}{dr} - \frac{i\omega P}{\mu}u = \frac{A}{\mu} \quad (20)$$

with boundary conditions at r=R, u=0, and at r=0, $$\frac{du}{dr} = 0.$$

To account for the arterial pulsatility, a triphasic waveform is modeled int the hepatic artery model, as given by $$7t^{2}e^{-\frac{t^2}{10}}\sin\left(\frac{2\pi t}{4}\right) + \frac{1}{20}\sin\left(\frac{2\pi t}{2}\right) + 0.06.$$

Using the foregoing equations to model physical attributes of blood flow and arterial response, a fluid flow model can be generated and simulations performed. The fluid flow simulation package (such as, e.g., COMSOL Multiphysics) can then be used to identify areas of low perfusion in the 3D "system" at block 510. For example, the pressure gradient within the arterial lumen, blood velocity, and dynamic viscosity of blood can be determined by using measured, patient-specific characteristics such as patient temperature and blood pressure, together with known averages. Then, estimated blood velocity can be calculated at each time slice for each location within the model, and used to show areas of low perfusion.

Figure 1:
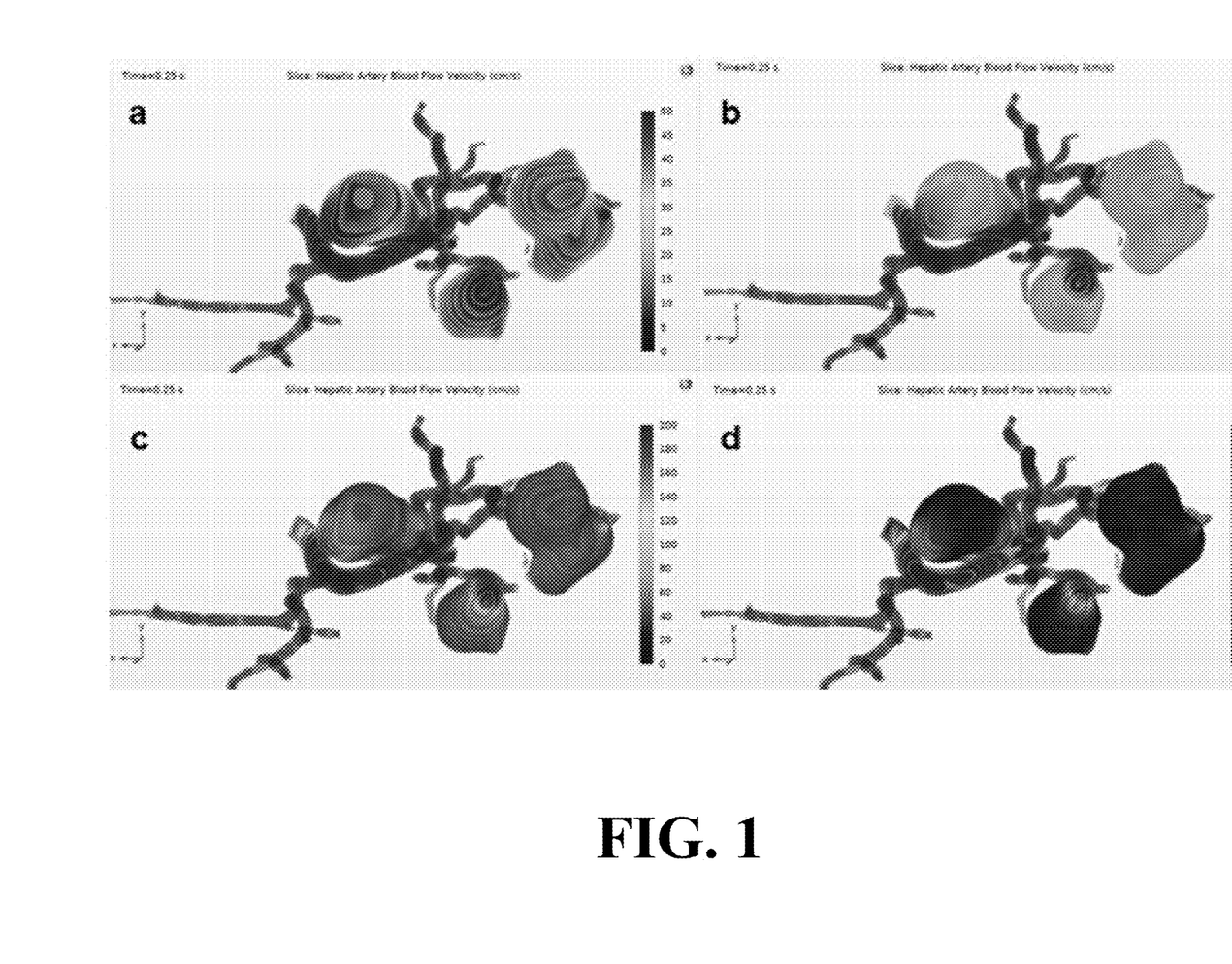
FIG. 1 is a posterior projection of hepatic neuroendocrine live metastases (NETLMs) and a feed arterial tree at various flow velocity thresholds.

This identification can be done automatically (e.g., a low perfusion threshold can be applied to highlight areas of the 3D system with a low perfusion; or a relative comparison can be made to highlight areas that are a given deviation lower in perfusion than most of the anatomy) or by a user through visual inspection (e.g., where the software platform color codes perfusion in a heat map style). For example, in embodiments in which blood velocity is simulated, areas in a 3D model may still exhibit velocity=0 or some other low value, implicating that there is decreased delivery of the intended therapy. At block 512, specific tumors or lesions of interest can be identified among the areas of low perfusion. Optionally, this identification can be part of the same step as block 510. Identification of low perfusion areas that correspond to tumors or lesions of interest can be done by manual observation of a summary image/model presented to a user (such as a radiologist or oncologist) or can automatically be done such as be a computer vision application that identifies anomalous volumes in the 3D system that correspond to tumors or lesions. FIG. 1 shows a series of "heat map" images in which arterial blood flow is shown for an arterial system/anatomy of interest. Each image is sequentially thresholded to highlight different simulated blood velocities. As can be see, certain "cold spots" exist wherein, in comparison to the highest blood flow rate determined, the "cold spots" receive relatively low blood flow (and, thus, can be interpreted as areas in which a blood-perfusion-delivered therapy is not reaching).

At step 514, a model of potential tumor recurrence can then be utilized to create a model overlay indicating to the patient's healthcare team of those tumors or lesions likely to exhibit recurrence of the patient's disease after the treatment regimen has concluded. In some embodiments, patient data from prior studies can be used to create a probabilistic model for tumor recurrence. Various parameters such as diagnosis, tumor dimensions and volume, degree of perfusion of a treatment into the tumor(s), and patient-specific attributes such as age, time since diagnosis, etc. can be regressed against tumor recurrence. Alternatively, at block 514, a mapping of low perfusion areas may be displayed to the user, to indicate areas within an anatomy of interest (e.g., a portion of a vascular region within the anatomy of interest that was part of the fluid flow system model) that are not likely receiving an optimal amount of a perfusion-based treatment. For example, the mapping may show that a suspected tumor within a portion of the anatomy of interest in the 3D visualization has a location that corresponds to a localized area of low perfusion/low blood flow. This can indicate to the user (e.g., an oncologist) that a specific suspected tumor or area of a tumor may not be adequately treated by a blood perfusion based treatment.

Figure 2A:
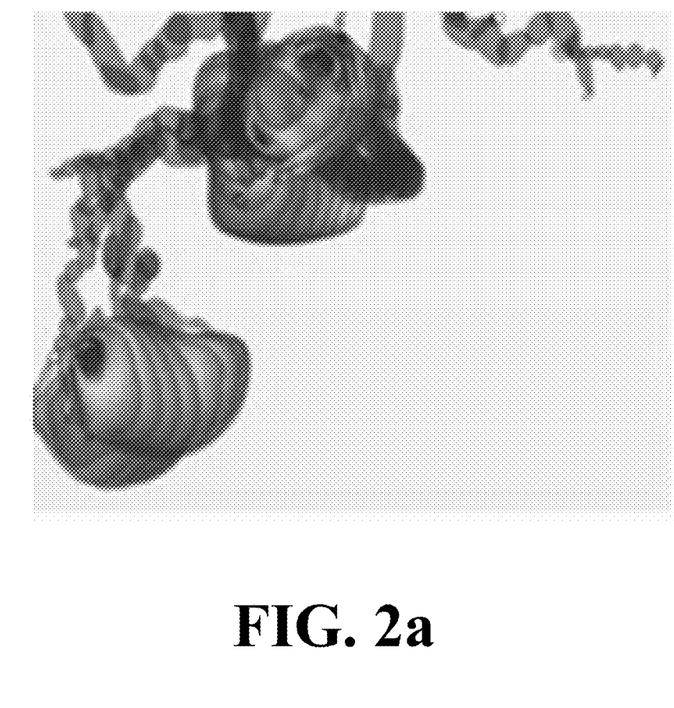
FIG. 2 is a late phase computed tomography angiography (CTA) model with a blood flow velocity threshold at 200 cm/s.
Figure 2B:
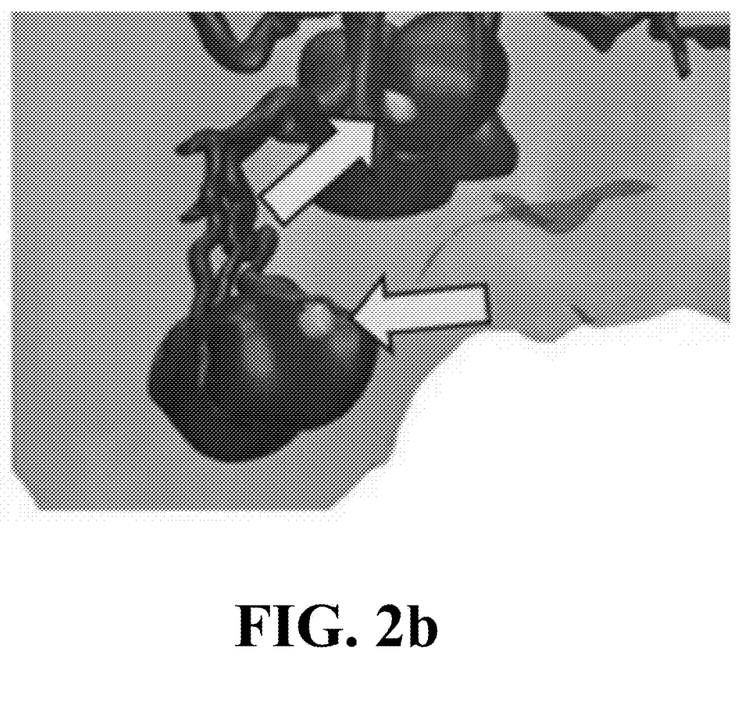
Figure 3A:
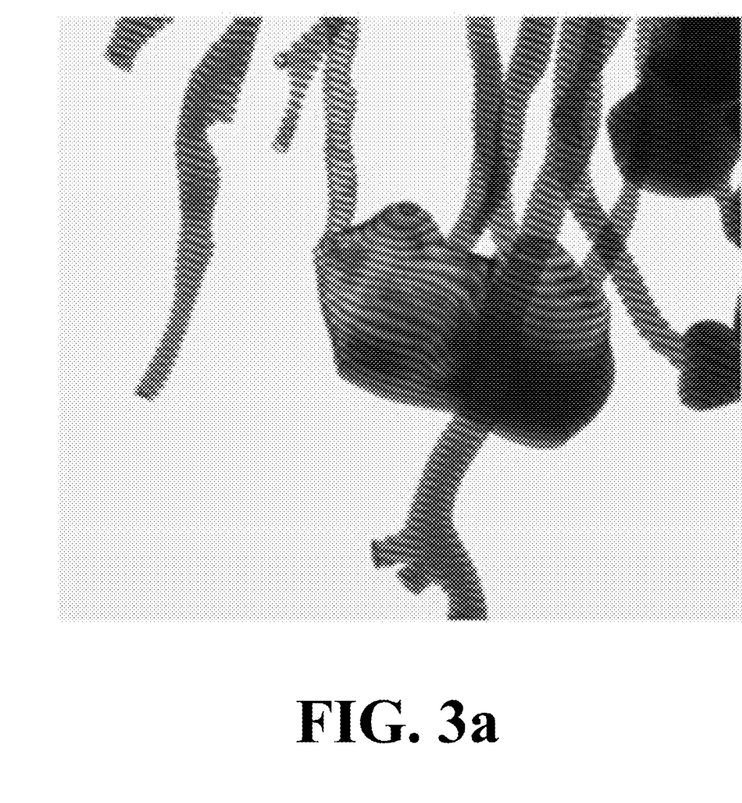
FIG. 3 is a model of a perfusion watershed region in between two supplying vessels.
Figure 3B:
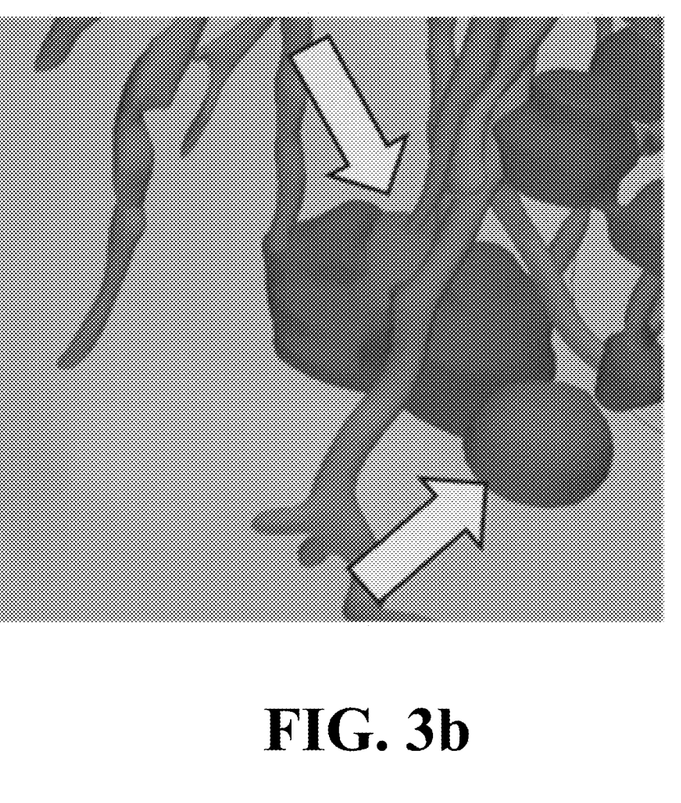

In studies performed by the inventor, a high correlation is exhibited between low perfusion rates and tumor recurrence for various disease types and locations. For example, in a study of patients with liver disease, low perfusion "cold spots" corresponding to tumors were identified, and hypothesized to be areas in which Y-90 radioembolization microspheres were not being deposited adequately based on blood flow distribution. Follow up scans confirmed that tumor recurrence correlated strongly with areas of low perfusion. FIG. 2 illustrates an example of such follow up exams, in which areas of relatively low blood flow (FIG. 2A) correlate to areas of subsequent tumor recurrence (FIG. 2B) FIG. 3A and FIG. 3B show similar incidences of "cold spots" correlating to future tumor recurrence sites.

Information indicative of potential recurrence of tumors and/or inadequate treatment can then be output to the patient's healthcare team. Using this information, alterative or modified interventions can then be taken to prevent such recurrence. For example, the system can recommend that certain tumor or lesion locations receive direct introduction (e.g., direct, local injection) of the treatment that has not been adequately perfusing to the locations, or that ablation or other alternatives be utilized at such locations.

Examples and Experiments

Six patients with NETLMs and who were candidates for Y-90 radioembolization were retrospectively reviewed. Pre-embolization mapping was carried out in the angiography suite of two target hepatic arteries with injections of Isovue-240® during intra-arterial CT angiography (CTA) on a Canon 4D Scanner, captured at 6 and 14 seconds to provide multiphasic images. Subsequent CTAs were deidentified and exported as DICOM images to Mimics and 3 Matic software packages, where the artery distal to the tip of the microcatheter placement was segmented and exported to COMSOL Multiphysics. From the intraprocedural nursing records, the patient's specific vital signs and physiologic parameters were parameterized in the model with the Monte Carlo simulation until a solution converged. Follow-up multiphase CTs were used to model tumor recurrence and a resultant model overlay was created.

Three patients in the initial group had significant necrosis within the treatment beds which significantly limited the visualization of recurrence secondary to architectural distortion. Of the remaining three patients, late-phase intraprocedural angiograms demonstrated significantly improve visualization of the tumor vascular beds in comparison to the early arterial phase. The tumor vascular beds and feeding arteries were effectively segmented and represented in the resultant geometry in the modeling software. Variant flow patterns were mapped in the distal feeding vessels, as well as in the vascular tumor beds. Four maximum velocity thresholds allowed potential areas of low perfusion or "cold spot" to be identified, where to the Y-90 radioembolization microspheres would not deposit adequately based upon blood flow distribution. Three-dimensional reconstructions of the six-month follow-up posttreatment multiphase CTs demonstrated tumor recurrence geometries which were then placed to overlap the vascular model geometry. Identified cold spots demonstrated areas of recurrence.

What is claimed is:

1. A patient-specific method for identifying areas of low perfusion in an anatomy of interest, the method comprising:
   receiving angiography data corresponding to the anatomy of interest within a patient;
   generating a three-dimensional (3D) model of the anatomy of interest, based on the angiography data;
   modifying the 3D model to represent a fluid flow system exhibiting variant flow patterns;
   ascribing physical characteristics to a simulation of the fluid flow system based on patient-specific data;
   determining at least one low perfusion area of the anatomy of interest; and
   outputting to a user an indication of potential tumor recurrence to a user display, based on determination of the at least one low perfusion area.

2. The method of claim 1, wherein the angiography data comprises data obtained from a computed tomography (CT) scanner during a CT angiography scan.

3. The method of claim 1, wherein the variant flow patterns exhibit areas of varying perfusion.

4. The method of claim 1, wherein the angiography data includes a plurality of images associated with one or more of a tumor vascular bed.

5. The method of claim 1, wherein, when the low perfusion area of the anatomy of interest corresponds to a tumor location, an indication is output to a user display indicating that a perfusion-based treatment is likely not adequately reaching the tumor location.

6. The method of claim 5, wherein a likelihood of tumor recurrence is determined for the tumor location based on the determination of the low perfusion area corresponding to the tumor location, and an indication of the likelihood of tumor recurrence is output to the user display.

7. The method of claim 1, wherein modifying the 3D model to represent a fluid flow system includes generating inflow and outflow apertures in the 3D model and defining vascular walls and lumens of the anatomy of interest.

8. The method of claim 1, wherein ascribing physical characteristics to the simulation further includes using patient-specific blood pressure, heart rate, and temperature measurements to define attributes of blood flow, blood viscosity, and arterial response to blood flow.

9. The method of claim 1, wherein ascribing physical characteristics to the simulation further includes using patient-specific blood pressure, heart rate, or temperature measurements to define attributes of blood flow, blood viscosity, or arterial response to blood flow.

10. A system for providing an indication of vascular tumor recurrence, comprising:
    a data link connected to receive angiography data for an anatomy of interest, acquired via an angiography scan of a patient;
    a medical image database connected to the data link and configured to store the angiography data;
    a processor connected to the database, and programmed to:
       obtain a three-dimensional computer model for a portion of the anatomy of interest comprising at least one suspected tumor, based on the angiography data;
       define a fluid flow model for the portion of the anatomy of interest, the fluid flow model configured to simulate perfusion within the portion of the anatomy of interest based on a blood viscosity estimation, a blood flow estimation, and a vascular wall elasticity estimation;
       determine whether a localized area of low perfusion within the portion of the anatomy of interest corresponds to a location of the suspected tumor and, if so, identify the suspected tumor as having a likelihood of recurrence; and
       output a mapping to a user via a display device, showing at least one of the localized area of low perfusion or the likelihood of recurrence for the suspected tumor, within the portion of the anatomy of interest.

11. The system of claim 10, wherein the angiography data comprises data obtained via a CT angiography scan of the patient.

12. The system of claim 11, wherein the angiography data comprises data obtained during a 14 second period of acquisition of the CT angiography scan.

13. The system of claim 10, wherein defining the fluid flow model includes defining inflow and outflow apertures for a vascular region of portion of the anatomy of interest, the vascular region comprising the suspected tumor.

14. The system of claim 13, wherein the blood viscosity and blood flow estimation are made based upon measured patient-specific characteristics.

15. The system of claim 14, wherein the patient-specific characteristics include at blood pressure, heart rate, and temperature.

16. The system of claim 15, wherein the blood flow estimation is modeled as a laminar flow.

17. The system of claim 13, wherein the blood viscosity or blood flow estimation are made based upon measured patient-specific characteristics.

18. The system of claim 17, wherein the patient-specific characteristics include at blood pressure, heart rate, or temperature.

19. The system of claim 18, wherein the blood flow estimation is modeled as a laminar flow.

* * * * *